(12) United States Patent
Kondo (10) Patent No.: US 10,416,320 B2
(45) Date of Patent: Sep. 17, 2019

(54) RADIOGRAPHIC IMAGING APPARATUS

(71) Applicant: CANON KABUSHIKI KAISHA, Tokyo (JP)

(72) Inventor: Hiroto Kondo, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/030,015

(22) PCT Filed: Oct. 8, 2014

(86) PCT No.: PCT/JP2014/076927
§ 371 (c)(1),
(2) Date: Apr. 15, 2016

(87) PCT Pub. No.: WO2015/056616
PCT Pub. Date: Apr. 23, 2015

(65) Prior Publication Data
US 2016/0299237 A1 Oct. 13, 2016

(30) Foreign Application Priority Data

Oct. 17, 2013 (JP) ................. 2013-216478

(51) Int. Cl.
*G01T 1/202* (2006.01)
*G03B 42/04* (2006.01)
*A61B 6/00* (2006.01)

(52) U.S. Cl.
CPC .......... *G01T 1/2023* (2013.01); *A61B 6/4208* (2013.01); *G01T 1/202* (2013.01); *G03B 42/04* (2013.01)

(58) Field of Classification Search
CPC ....... G01T 1/2023; G01T 1/202; G03B 42/04; A61B 6/4208
See application file for complete search history.

(56) References Cited

U.S. PATENT DOCUMENTS

| 3,884,818 | A | * | 5/1975 | Tomita | ................... | G03B 42/04 378/187 |
| RE30,045 | E | * | 7/1979 | Greene | ................... | G03B 42/04 206/455 |
| 6,411,672 | B1 | * | 6/2002 | Sasaki | ................... | A61B 6/035 250/370.15 |

(Continued)

FOREIGN PATENT DOCUMENTS

| CN | 101133961 A | 3/2008 |
| JP | H10-177224 A | 6/1998 |

(Continued)

*Primary Examiner* — Christine S. Kim
(74) *Attorney, Agent, or Firm* — Canon U.S.A., Inc. IP Division (57) ABSTRACT

To provide a radiographic imaging apparatus having an airtight internal space and capable of reducing a difference in air pressure between the inside and the outside thereof, a radiographic imaging apparatus includes a radiation detector configured to detect radiation transmitted through an object to be examined and convert the radiation into an electrical signal, and sealing members configured to seal an opening in a housing of the apparatus, wherein the sealing members have the function of reducing a difference in air pressure between the inside and the outside of the housing.

21 Claims, 8 Drawing Sheets

(56) References Cited

U.S. PATENT DOCUMENTS

| | | | |
|---|---|---|---|
| 7,482,595 B1* | 1/2009 | Ertel | G01T 1/2018 250/370.09 |
| 7,909,510 B2 | 3/2011 | Ohta | |
| 9,354,326 B2* | 5/2016 | MacLaughlin | G01T 1/00 |
| 2003/0010925 A1* | 1/2003 | Watanabe | G01T 1/2928 250/370.15 |
| 2008/0054182 A1 | 3/2008 | Yokoyama | |
| 2009/0154648 A1* | 6/2009 | Watanabe | A61B 6/4216 378/116 |
| 2009/0323900 A1* | 12/2009 | Ohta | A61B 6/585 378/167 |
| 2010/0243894 A1* | 9/2010 | Kato | G01T 7/00 250/336.1 |
| 2011/0310194 A1* | 12/2011 | Takagi | B41J 2/17509 347/86 |
| 2012/0069966 A1* | 3/2012 | Kobayashi | A61B 6/00 378/189 |
| 2012/0138798 A1* | 6/2012 | Kato | H01L 27/14618 250/336.1 |
| 2013/0105696 A1* | 5/2013 | Shaw | G21K 4/00 250/361 R |

FOREIGN PATENT DOCUMENTS

| | | | |
|---|---|---|---|
| JP | 2000-258541 A | | 9/2000 |
| JP | 2003-21642 A | | 1/2003 |
| JP | 2008-83031 A | | 4/2008 |
| JP | 2010085266 A | | 4/2010 |
| JP | 2011-47737 A | | 3/2011 |
| JP | 2011047737 A | * | 3/2011 |
| JP | 2011-69992 A | | 4/2011 |
| JP | 2012-040072 A | | 3/2012 |
| JP | 2012-181044 A | | 9/2012 |
| JP | 5265480 B2 | | 8/2013 |
| RU | 2276578 C1 | | 5/2006 |

\* cited by examiner

RADIOGRAPHIC IMAGING APPARATUS

CROSS-REFERENCE TO RELATED APPLICATIONS

This application is a National Stage filing of International Application No. PCT/JP2014/076927 filed Oct. 8, 2014, which claims the benefit of Japanese Patent Application No. 2013-216478 filed Oct. 17, 2013, the disclosures of each of which are hereby incorporated by reference herein in their entirety.

TECHNICAL FIELD

The present invention relates to a radiographic imaging apparatus configured to detect radiation transmitted through an object to be examined and convert the radiation into an electrical signal.

BACKGROUND ART

In the field of medicine, with recent advances in semiconductor processing technology, the use of radiographic imaging apparatuses that capture a radiographic image using a semiconductor sensor has become widespread. The radiographic imaging apparatuses have a much wider dynamic range than conventional radiographing systems using a photographic sensitive film, and can produce a radiographic image which is not affected by variation in the amount of exposure to radiation.

The radiographic imaging apparatuses are expected to be used in a wide variety of situations, and are used not only in general radiographic rooms but also for ward rounds and emergency care. Since such a radiographic imaging apparatus is often used in direct contact with patients of various conditions, the radiographic imaging apparatus is cleaned, disinfected, and sterilized after use. For the purposes of disinfection and sterilization, not only water but also a liquid containing an organic solvent or a disinfectant is often used.

For airtightness of the radiographic imaging apparatus, Patent Literature 1 discloses a technique in which there is a lid member that fits in an opening, and a waterproof member is provided at a connection between a housing and the lid member. Patent Literature 2 shows that if there is air in a closed space of the radiographic imaging apparatus, the airtightness of the radiographic imaging apparatus is changed by changes in air pressure outside the closed space.

CITATION LIST

Patent Literature

PTL 1: Japanese Patent Laid-Open No. 2012-181044
PTL 2: Japanese Patent Laid-Open No. 2011-69992

SUMMARY OF INVENTION

Technical Problem

In the radiographic imaging apparatus that requires airtightness as described above, the opening in the outer periphery of the housing is provided with a sealing member. However, increasing the airtightness of the radiographic imaging apparatus blocks passage of air between the inside and the outside of the apparatus, and changes in outside air pressure may lead to changes in the shape of the radiographic imaging apparatus.

The present invention has been made to solve the problems describe above. An object of the present invention is to provide a radiographic imaging apparatus having an airtight internal space and capable of reducing a difference in air pressure between the inside and the outside thereof.

Solution to Problem

To achieve the object of the present invention, a radiographic imaging apparatus including a radiation detector configured to detect radiation transmitted through an object to be examined and convert the radiation into an electrical signal includes a sealing member configured to seal an opening in a housing of the apparatus, wherein the sealing member has the function of reducing a difference in air pressure between the inside and the outside of the housing.

Advantageous Effects of Invention

The radiographic imaging apparatus according to the present invention has an airtight internal space and is capable of reducing a difference in air pressure between the inside and the outside thereof.

DESCRIPTION OF EMBODIMENTS

Preferred embodiments of the present invention will now be described with reference to the attached drawings.

First Embodiment

Figure 1:
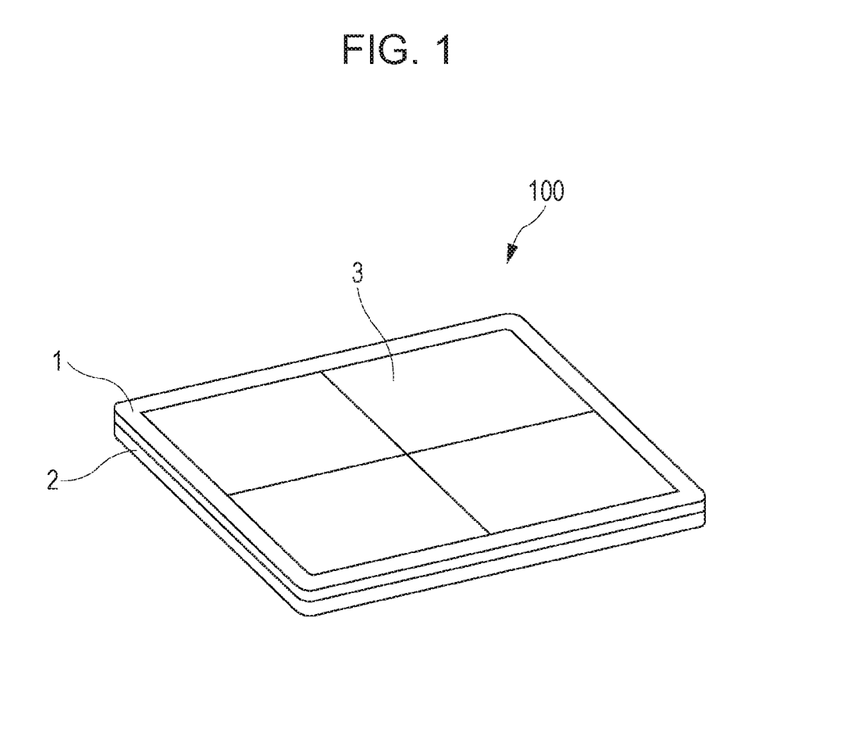
FIG. 1 illustrates an appearance (radiation incident side) of a radiographic imaging apparatus according to a first embodiment of the present invention.

FIG. 1 illustrates an appearance (radiation incident side) of a radiographic imaging apparatus 100 according to a first embodiment of the present invention. The exterior of the radiographic imaging apparatus 100 is formed by a housing having a large opening for incidence of radiation. The housing includes a front housing 1 on the radiation incident side and a back housing 2 on the back side. The radiographic imaging apparatus 100 includes a radiation transmitting plate 3 disposed in the opening in the front housing 1 and made of a radiation transmitting material. A high-stiffness material, such as a light-weight high-strength aluminum alloy or magnesium alloy, is used to form the front housing 1 and the back housing 2. The front housing 1 and the back housing 2 cover the outer part of the radiographic imaging apparatus 100 to protect the internal components of the radiographic imaging apparatus 100.

The radiographic imaging apparatus 100 includes a radiation detector (hereinafter referred to as "sensor") therein. The sensor is formed by stacking fluorescent members that receive radiation transmitted through an object to be examined and convert the radiation into light. The sensor is configured to convert the light into an electrical signal.

Figure 2:
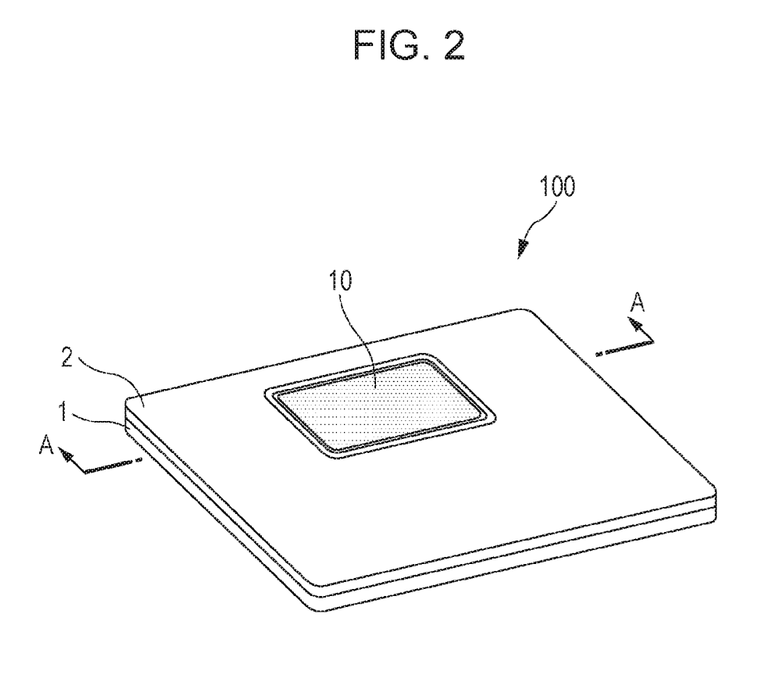
FIG. 2 illustrates an appearance (back side) of the radiographic imaging apparatus according to the first embodiment of the present invention.

FIG. 2 illustrates an appearance (back side) of the radiographic imaging apparatus 100 according to the first embodiment of the present invention. The back housing 2 has an opening of a predetermined size. A cover member 10 is detachably attached to the back housing 2 to fill in the opening. The opening can be used as a space that allows access to an electrical substrate inside the radiographic imaging apparatus 100, or as a space for a battery when the radiographic imaging apparatus 100 is of a wireless type. That is, a battery for supplying power is placed in the opening in the back housing 2, and the battery is protected by the cover member 10. The back housing 2 is flat when the cover member 10 is attached thereto.

Figure 3:
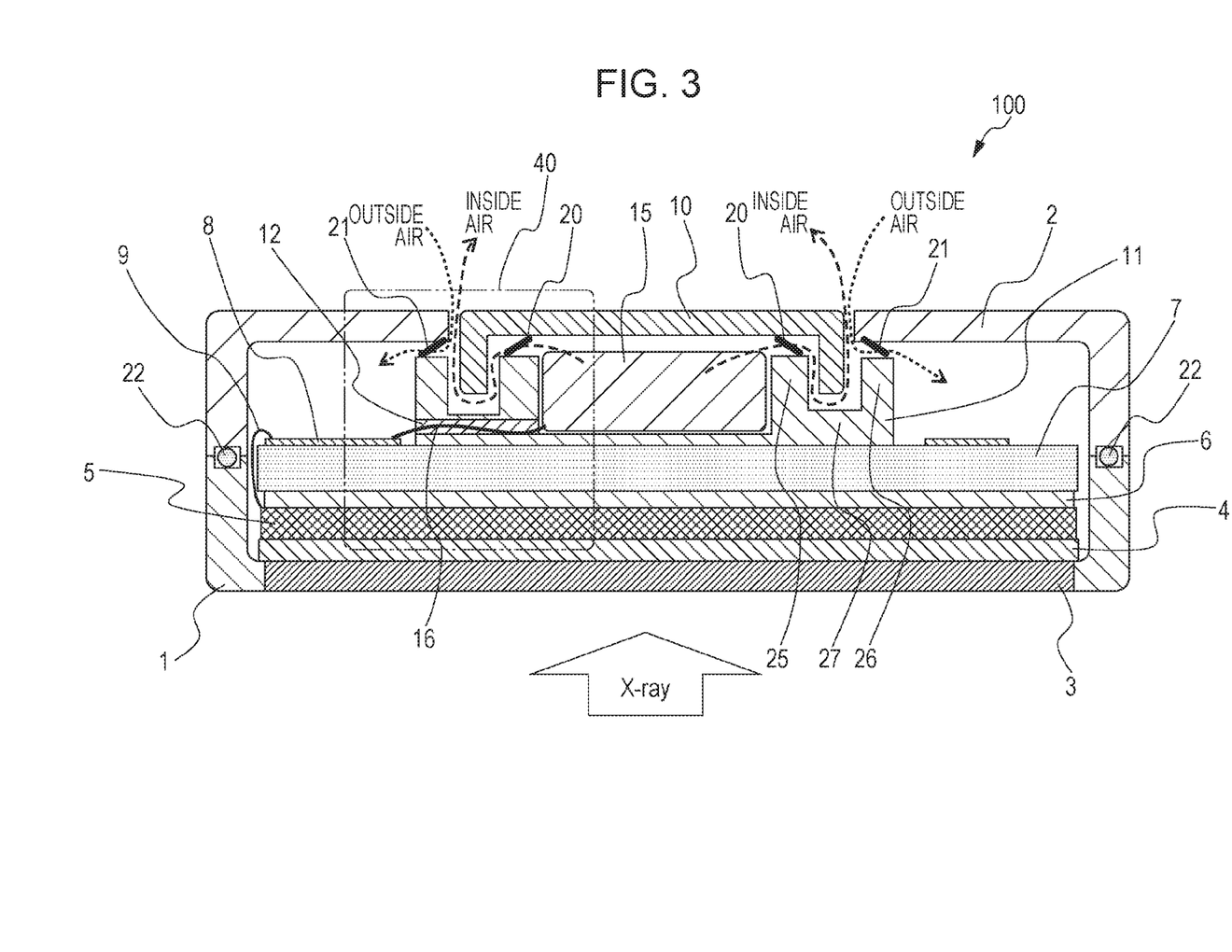
FIG. 3 illustrates an internal structure of the radiographic imaging apparatus according to the first embodiment of the present invention.

FIG. 3 illustrates an internal structure of the radiographic imaging apparatus according to the first embodiment of the present invention. FIG. 3 is a cross-sectional view taken along line A-A of FIG. 2.

The front housing 1 on the radiation incident side is provided with the radiation transmitting plate 3 that transmits radiation. The radiation transmitting plate 3 serves as a support member to be subjected to a load from the object placed on the radiation incident side.

A shock absorbing member 4 (protective sheet) that absorbs shocks is disposed between a sensor 5 and the radiation transmitting plate 3. Even if the radiation transmitting plate 3 warps under a load from the object, the sensor 5 can be protected by the shock absorbing member 4.

The sensor 5 is formed by stacking fluorescent members that receive radiation transmitted through the object and convert the radiation into light, and is configured to convert the light into an electrical signal. The sensor 5 is disposed on a sensor retaining plate 7, with a radiation shielding member 6 interposed therebetween. The radiation shielding member 6 is a shielding member configured to block radiation. The radiation shielding member 6 blocks radiation from propagating from the sensor 5 toward electrical substrates 8 (back housing 2).

Typically, GOS (Gd2O2S) or CsI is used as a material for the fluorescent members stacked to form the sensor 5. The electrical substrates 8 are attached to a surface of the sensor retaining plate 7 opposite the surface on which the sensor 5 is disposed. The electrical substrates 8 are configured to process the electrical signal obtained by conversion in the sensor 5, and generate image data. The generated image data is transmitted to and displayed by an external display unit (not shown). The image data is transmitted either through wires or wirelessly. In the case of wireless transmission, a 2.4 GHz or 5 GHz band is primarily used.

A flexible cable is used for connection between the electrical substrates 8 and between the electrical substrates 8 and other components. Specifically, the sensor 5 and the electrical substrates 8 are connected to each other by a flexible cable 9, so that the electrical substrates 8 can receive an electrical signal obtained by conversion in the sensor 5. The electrical substrates 8 and the battery 15 are connected to each other by a flexible cable 16. The electrical substrates 8 can supply power from the battery 15 to the sensor 5.

When the radiographic imaging apparatus 100 is of a wireless cassette type, the battery 15 needs to be included for driving the radiographic imaging apparatus 100. A battery holder 11 configured to hold the battery 15 is disposed in the opening in the back housing 2. The inside of the radiographic imaging apparatus 100 (the inside of the housing) is an interior surrounded by the front housing 1 and the back housing 2. The battery holder 11 is configured to fit in the opening in the back housing 2, and is positioned to correspond to the opening. The battery holder 11 is disposed on the sensor retaining plate 7. Specifically, the battery holder 11 is disposed on the surface of the sensor retaining plate 7 opposite the surface on which the sensor 5 is disposed.

The battery holder 11 has a space configured to contain and hold the battery 15, and a groove portion 27 configured to contain an end portion of the cover member 10. Specifically, the battery holder 11 has a bottom portion in contact with the sensor retaining plate 7, an inner wall 25 extending vertically from the bottom portion and covering the periphery of the battery 15, and an outer wall 26 extending vertically from the bottom portion and forming the inner wall 25 and the groove portion 27. The inner wall 25 and the outer wall 26 are in the shape of a substantially rectangular ring.

The space that contains and holds the battery 15 is formed by the inner wall 25. The height of the inner wall 25 is substantially the same as the height of the contained battery 15. A lithium-ion battery is typically used as the battery 15, but the battery 15 is not limited to this.

The outer wall 26 is formed along the outer periphery of the inner wall 25. The groove portion 27 is also formed along the outer periphery of the inner wall 25. The inner wall 25 is positioned to allow the cover member 10 to be disposed on the upper side of the inner wall 25. The outer wall 26 is positioned to allow the back housing 2 to be disposed on the upper side of the outer wall 26. The end portion of the cover member 10 is contained in the groove portion 27.

The battery holder 11 has a through hole 12, which allows passage of air from the side of the electrical substrates 8 to the side of the battery 15. The through hole 12 allows the flexible cable 16 to be placed therein, and allows the electrical substrates 8 to be electrically connected to the battery 15.

The radiographic imaging apparatus 100 includes the radiation detector (sensor 5) configured to detect radiation transmitted through the object and convert the radiation into an electrical signal, and sealing members 20 and 21 configured to seal the opening in the housing of the apparatus. The sealing members 20 and 21 have the function of reducing a difference in air pressure between the inside and the outside of the housing. Here, the sealing member 20 may be defined as a first sealing member, and the sealing member 21 may be defined as a second sealing member. The sealing members 20 and 21 have the function of allowing passage of air in a predetermined direction. The housing and the sealing members 20 and 21 form an air circulation cycle inside the housing.

For attachment and detachment of the battery 15, the cover member 10 can be attached to and detached from the radiographic imaging apparatus 100. The sealing member 20 is disposed inside (or on the bottom side of) the cover member 10 covering the opening. That is, the sealing member 20 is disposed on the side of the cover member 10 facing the battery holder 11.

The sealing member 20 has the function of not only sealing the opening in the radiographic imaging apparatus 100 (housing), but also reducing a difference in air pressure between the inside and the outside of the housing. When the cover member 10 is attached to the opening, the sealing member 20 is brought into contact with the battery holder 11. Specifically, the sealing member 20 on the cover member 10 is brought into contact with the upper surface of the inner wall 25 of the battery holder 11. The sealing member 20 disposed along the inner periphery of the cover member 10 is in contact with the battery holder 11 along an edge of the upper surface of the inner wall 25. Thus, the battery side of the battery holder 11 is sealed by the sealing member 20.

The sealing member 20 is a valve (valve-shaped member). The battery holder 11 and the sealing member 20 form a valve function that allows passage of air in a predetermined direction. The sealing member 20 does not require a relatively large compressive force. By using a valve as the sealing member 20, airtightness can be ensured with a relatively small compressive force. Additionally, with the sealing member 20, air inside the housing (inside air) can be discharged to the outside of the housing.

In other words, the sealing member 20 is configured to be compressed between the cover member 10 and the battery holder 11. The sealing member 20 and the battery holder 11 allow air to pass therebetween in the predetermined direction. Specifically, air can pass from the inside to the outside of the housing, whereas passage of air from outside the housing is blocked. It is thus possible to prevent entry of light and water from outside the housing.

With the sealing member 20, which is a valve (valve-shaped member), air can pass from the region of higher air pressure to the region of lower air pressure when a difference in air pressure between the inside and the outside of the radiographic imaging apparatus 100 (housing) occurs. That is, a difference in air pressure between the inside and the outside of the housing can be reduced.

The sealing member 21 is disposed inside (or on the bottom side of) the housing (back housing 2). That is, the sealing member 21 is disposed on the side of the back housing 2 facing the battery holder 11.

The sealing member 21 has the function of not only sealing the opening in the radiographic imaging apparatus 100 (housing), but also reducing a difference in air pressure between the inside and the outside of the housing. When the back housing 2 is attached to the front housing 1 with screws, the sealing member 21 is brought into contact with the battery holder 11. Specifically, the sealing member 21 on the back housing 2 is brought into contact with the upper surface of the outer wall 26 of the battery holder 11. The sealing member 21 disposed along the inner periphery of the back housing 2 is in contact with the battery holder 11 along an edge of the upper surface of the outer wall 26. Thus, the interior of the housing (on the side of the electrical substrates 8) is sealed by the sealing member 21.

Like the sealing member 20, the sealing member 21 is a valve (valve-shaped member). The outer wall 26 of the battery holder 11 and the sealing member 21 form a valve function that allows passage of air in a predetermined direction. The sealing member 21 does not require a relatively large compressive force. By using a valve as the sealing member 21, airtightness can be ensured with a relatively small compressive force. Additionally, with the sealing member 21, air inside the housing (outside air) can be taken into the housing.

In other words, the sealing member 21 is configured to be compressed between the back housing 2 and the battery holder 11. The sealing member 21 and the back housing 2 allow air to pass therebetween in the predetermined direction. Specifically, air can pass from the outside to the inside of the housing.

With the sealing member 21, which is a valve (valve-shaped member), air can pass from the region of higher air pressure to the region of lower air pressure when a difference in air pressure between the inside and the outside of the radiographic imaging apparatus 100 (housing) occurs. That is, a difference in air pressure between the inside and the outside of the housing can be reduced.

The sealing member 20 and the sealing member 21, which are valves, are inclined in the same direction. As illustrated in FIG. 3, the sealing member 20 and the sealing member 21 are formed to be inclined downward with distance from the center of the cover member 10.

The sealing member 21 allows passage of outside air into the housing, whereas the sealing member 20 allows passage of inside air to the outside of the housing. To enable both the sealing of the housing and the passage of air, a space (opening) formed by the battery holder 11 and the cover member 10 is spatially connected to the interior of the housing through the through hole 12.

If the sealing member 20 is disposed on the cover member 10 to be inclined downward toward the center of the cover member 10 whereas the sealing member 21 is inclined downward with distance from the center of the cover member 10, inside air cannot be discharged to the outside of the housing whereas outside air can enter the housing.

As in the present embodiment, when the sealing member 20 and the sealing member 21 are inclined in the same direction, a difference in air pressure between the inside and the outside of the housing can be reduced.

Although valves are used as the sealing member 20 and the sealing member 21 in the present embodiment, the shape and locations of the sealing members are not particularly limited. The sealing member 20 and the sealing member 21 may be disposed on the battery holder 11.

Although the sealing member 20 and the sealing member 21 are inclined leftward in the present embodiment, they may be inclined rightward as long as they are inclined in the same direction.

The flow direction of outside air and the flow direction of inside air may be changed by taking into account the location of a heating element inside the housing. If the amount of heat generated by the sensor 5 or the electrical substrates 8 is higher than that of the other components, the sealing member 21 is disposed in an orientation which allows discharge of inside air to the outside. If the amount of heat generated by the battery 15 is higher than that of the other internal components, the sealing member 20 is disposed in an orientation which allows discharge of inside air to the outside. Efficient heat dissipation can thus be achieved by positioning the sealing member 20 and the sealing member 21 as described above.

Figure 4:
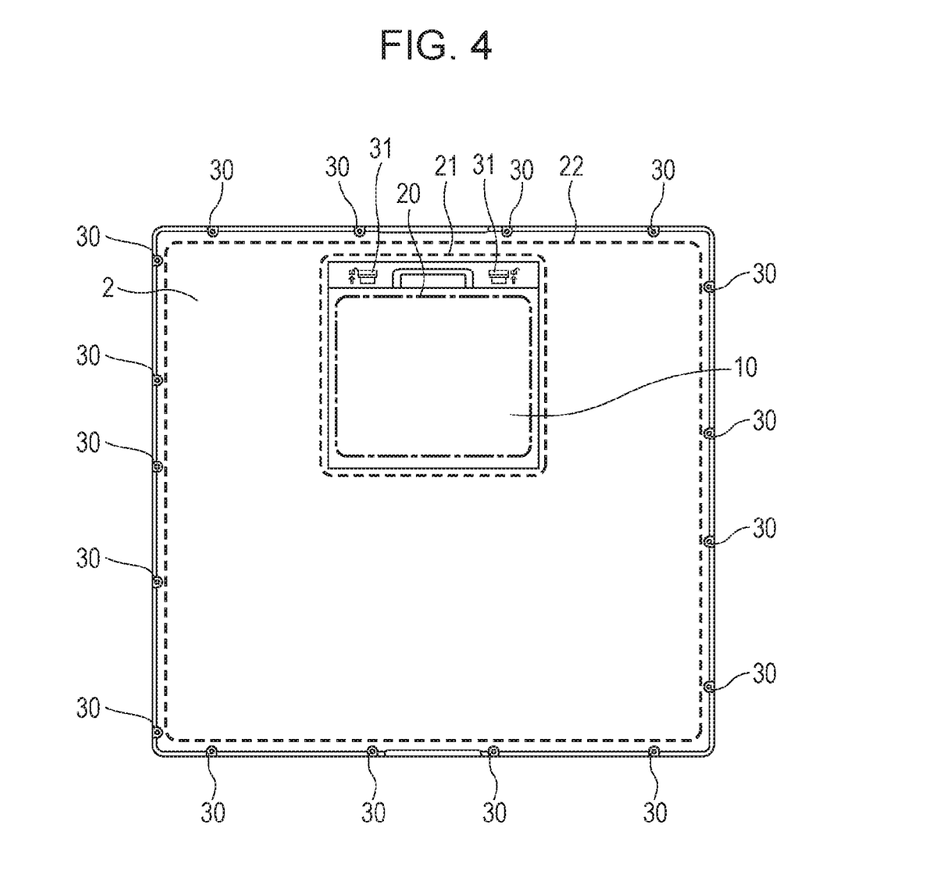
FIG. 4 illustrates an upper side (back side) of the radiographic imaging apparatus according to the first embodiment of the present invention.

FIG. 4 illustrates an upper side (back side) of the radiographic imaging apparatus 100 according to the first embodiment of the present invention. FIG. 4 illustrates how the sealing members are arranged. In FIG. 4, the locations of the sealing members are indicated by broken lines.

As illustrated in FIG. 4, the sealing member 20 is disposed inside (or on the bottom side of) the cover member 10 and extends along the edge of the cover member 10. The cover member 10 is a lid member. The sealing member 20 is disposed inside (or on the bottom side of) the outer edge of the cover member 10. That is, the sealing member 20 is disposed on the bottom side of the cover member 10, along the periphery of the cover member 10. The sealing member 20 is in the shape of a substantially rectangular ring.

When the cover member 10 is fastened with screws, the cover member 10 cannot be easily attached and detached, and hence it takes time to replace the battery 15. Accordingly, instead of using a technique which requires a high fastening force, such as fastening with screws, a plurality of easily detachable locking members 31 are used here.

The cover member 10 is secured in place by inserting the locking members 31 of the battery holder 11 into holes (not shown) in the cover member 10. The battery holder 11 has at least one locking member 31. The battery holder 11 has a pair of locking members 31 in the present embodiment. It is preferable that a plurality of locking members 31 be provided. When the locking members 31 are independently slidable, it is possible to prevent the locking members 31 from being accidentally unlocked, and to lower the risk of falling of the cover member 10 and the battery 15. The sliding direction of the locking members 31 is not limited, and may be set appropriately. The cover member 10 is thus secured to the radiographic imaging apparatus 100 (housing) with the locking members 31.

As illustrated in FIG. 4, the sealing member 21 is disposed along the edge of the opening in the housing (back housing 2). The housing has the opening for attachment of the cover member 10. The opening in the housing has substantially the same size as the cover member 10.

The sealing member 21 is disposed inside (or on the bottom side of) the area outside the opening in the housing. That is, the sealing member 21 is disposed on the bottom side of the housing, along the edge of the opening in the housing. The sealing member 21 is in the shape of a substantially rectangular ring.

As illustrated in FIG. 4, the front housing 1 and the back housing 2 are coupled to each other with a plurality of screws 30. All sides are provided with the same number of screws. Here, the front housing 1 and the back housing 2 are coupled to each other with 17 screws. As illustrated in FIG. 3, the front housing 1 and the back housing 2 are coupled to each other, with a sealing member 22 interposed therebetween. The sealing member 22 is disposed at a connection between the front housing 1 and the back housing 2. The sealing member 22 may be defined as a third sealing member. As illustrated in FIG. 4, the sealing member 22 is disposed inside the plurality of screws 30, in the front housing 1 or the back housing 2. The sealing member 22 is in the shape of a substantially rectangular ring.

The sealing member 22 has a high compressive force. For example, the sealing member 22 is a gasket, such as an O ring. When the front housing 1 and the back housing 2 are coupled to each other by fastening with the screws 30, the sealing member 22 can be compressed by a desired amount. This prevents air from leaking through the space between the front housing 1 and the back housing 2.

That is, the sealing member 22 is provided to enhance airtightness of the radiographic imaging apparatus 100 (housing). The sealing member 22 does not have the function of reducing a difference in air pressure between the inside and the outside of the housing. That is, the sealing member 22 has a function different from that of the sealing members 20 and 21.

Figure 5:
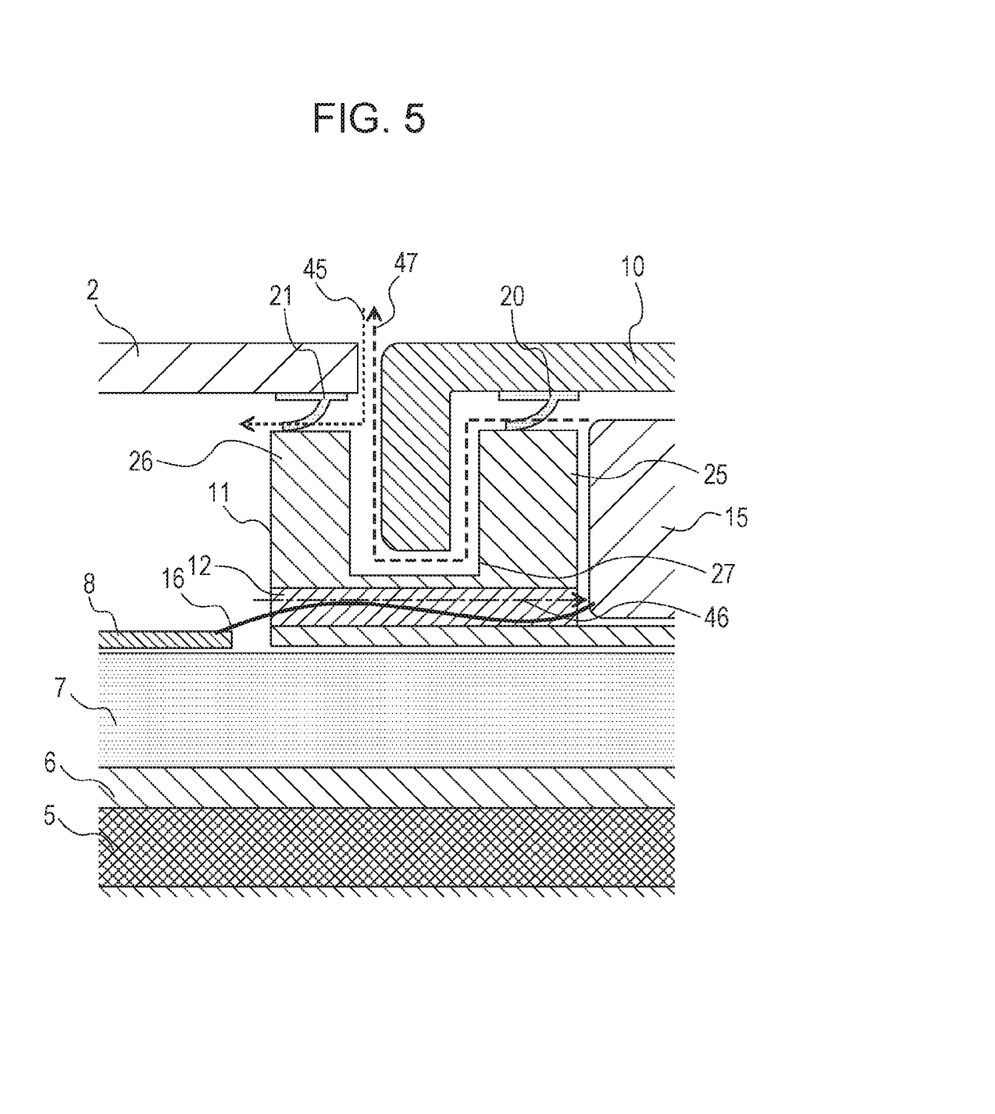
FIG. 5 illustrates a part of the internal structure of the radiographic imaging apparatus according to the first embodiment of the present invention.

FIG. 5 illustrates a part of the internal structure of the radiographic imaging apparatus 100 according to the first embodiment of the present invention. FIG. 5 particularly illustrates a range 40 in FIG. 3. Airflows in the housing are indicated by arrows 45 to 47.

The sealing member 21 includes an attached portion attached to the back housing 2, and an elastic portion inclined in a predetermined direction. The attached portion may be integral with the elastic portion.

The elastic portion of the sealing member 21 is inclined toward the outside of the housing. Attaching the back housing 2 to the front housing 1 brings the elastic portion into contact with the battery holder 11. Specifically, the elastic portion is brought into contact with the upper surface of the outer wall 26 of the battery holder 11. Bringing the elastic portion into contact with the battery holder 11 causes the elastic portion to bend outward. That is, the sealing member 21 bends outward.

There is a gap between the back housing 2 and the cover member 10, which allows passage of air. When air is taken in from outside the housing, the air passes through the gap between the back housing 2 and the cover member 10. Since the elastic portion of the sealing member 21 is inclined outward, the elastic portion of the sealing member 21 is raised by air taken in from outside. As indicated by the arrow 45, air can pass from the outside to the inside of the housing, but cannot pass from the inside to the outside of the housing. Air taken in from outside the housing temporarily moves to the interior of the housing where there are the electrical substrates 8.

The battery holder 11 has the through hole 12, through which the space where there are the electrical substrates 8 communicates with the space where there is the battery 15. The through hole 12 allows passage of air from the outside to the inside of the battery holder 11. That is, as indicated by the arrow 46, air in the interior (space) of the housing where there are the electrical substrates 8 can be moved to the opening (space) where there is the battery 15.

The sealing member 20 includes an attached portion attached to the cover member 10, and an elastic portion inclined in a predetermined direction. The attached portion may be integral with the elastic portion.

The elastic portion of the sealing member 20 is inclined toward the outside of the housing. The elastic portion of the sealing member 20 is brought into contact with the battery holder 11. Specifically, the elastic portion of the sealing member 20 is brought into contact with the upper surface of the inner wall 25 of the battery holder 11. Bringing the elastic portion of the sealing member 20 into contact with the battery holder 11 causes the elastic portion of the sealing member 20 to bend outward. That is, the sealing member 20 bends outward.

There is a gap between the battery holder 11 and the cover member 10, which allows passage of air. When air is discharged from the inside of the housing, the air passes through the gap between the battery holder 11 and the cover member 10. Since the elastic portion of the sealing member 20 is inclined outward, the elastic portion of the sealing member 20 is raised by air taken in from outside. As indicated by the arrow 47, air can pass from the inside to the outside of the housing.

As indicated by the arrows 45 to 47, the airflows in the housing can form an air circulation cycle. With the sealing member 21, which is a valve (valve-shaped member), air can pass from the region of higher air pressure to the region of lower air pressure when a difference in air pressure between the inside and the outside of the housing occurs.

For example, when the air pressure inside the housing is lowered, since the elastic portion of the sealing member 21 on the back housing 2 is inclined outward, air can pass from the outside to the inside of the housing as indicated by the arrow 45. Also, when the air pressure inside the housing is raised, since the elastic portion of the sealing member 20 on the cover member 10 is inclined outward, air can pass from the inside to the outside of the housing as indicated by the arrow 47. With this air circulation cycle in a predetermined direction in the radiographic imaging apparatus 100 (housing), a difference in air pressure between the inside and the outside of the radiographic imaging apparatus 100 (housing) can be reduced.

As described above, the present embodiment includes the sealing members 20 and 21 configured to seal the opening in the housing of the apparatus, and the sealing members 20 and 21 have the function of reducing a difference in air pressure between the inside and the outside of the housing. The sealing members 20 and 21 are valves, which allow passage of air in a predetermined direction. The sealing members 20 and 21 are valves, which are raised by a difference in air pressure between the inside and the outside of the housing. The sealing members 20 and 21 have a waterproof function.

The present embodiment includes the opening in the housing of the apparatus, and the detachable cover member 10 attached to the opening. The sealing member 20 is disposed inside the cover member 10, and the sealing member 21 is disposed in the opening in the housing. The sealing member 20 and the sealing member 21 are in contact with a component in the housing.

The opening in the housing of the apparatus is provided with the sealing member 20 and the sealing member 21 configured to seal the opening. The sealing member 20 and the sealing member 21 are valves, which allow passage of air in a predetermined direction. The sealing member 20 and the sealing member 21, which are valves, are inclined in the same direction.

The present embodiment includes the opening in the housing of the apparatus, and the detachable cover member 10 attached to the opening. The sealing member 20 is disposed inside the cover member 10, and the sealing member 21 is disposed inside the housing. The sealing member 20 and the sealing member 21 are in contact with a component disposed in the housing, and are configured to seal the housing and allow passage of air in a predetermined direction.

Although the component described above is the battery holder 11 in the present embodiment, the component does not necessarily need to be the battery holder 11.

If there is no difference in air pressure between the inside and the outside of the radiographic imaging apparatus 100 (housing), the sealing members 20 and 21 do not allow air to circulate. That is, since the radiographic imaging apparatus 100 (housing) is sealed by the sealing members 20 and 21, the waterproofness of the radiographic imaging apparatus 100 (housing) can be maintained.

A second embodiment of the present invention will now be described with reference to FIGS. 6 to 8. The second embodiment differs from the first embodiment in that a sealing member 61 disposed between the front housing 1 and the back housing 2 forms an air circulation cycle.

Figure 6:
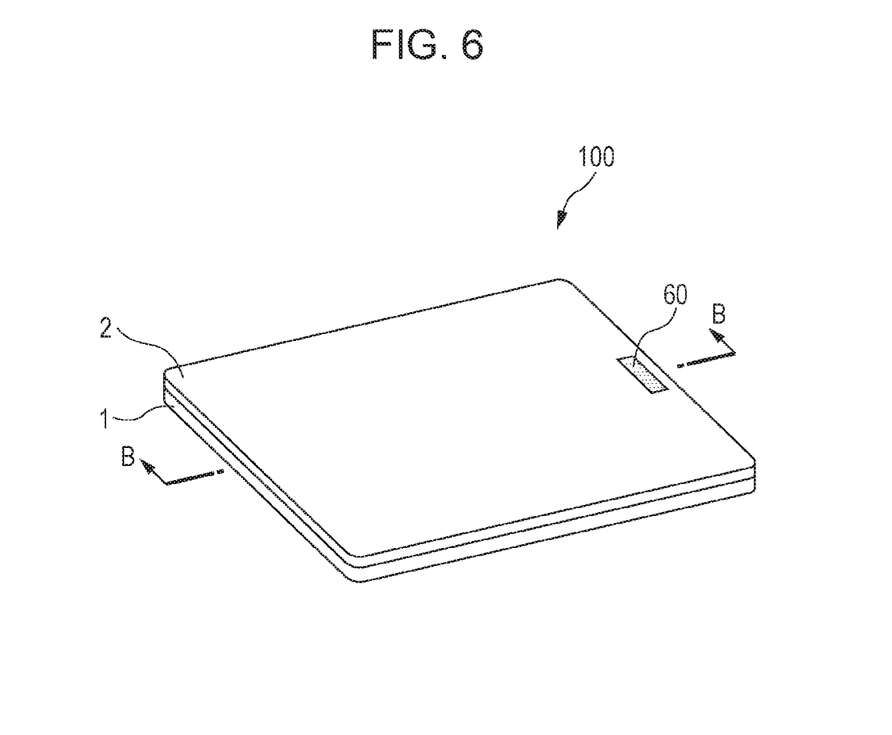
FIG. 6 illustrates an appearance (back side) of a radiographic imaging apparatus according to a second embodiment of the present invention.
Figure 7:
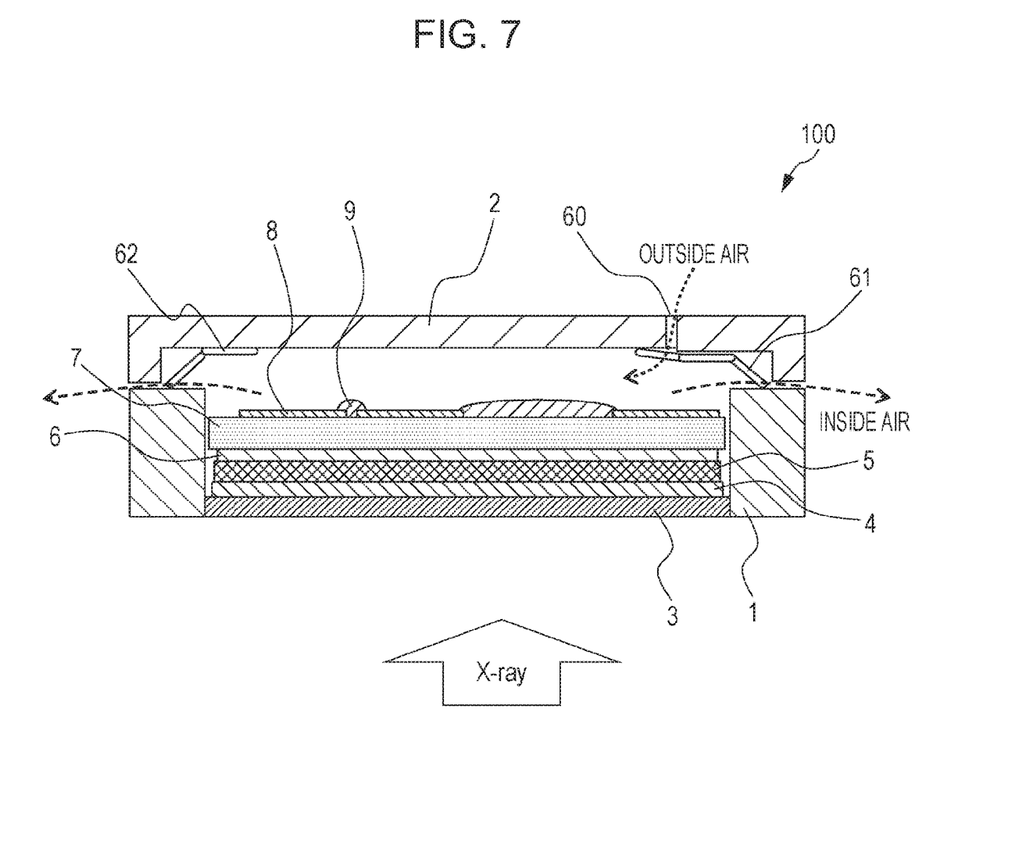
FIG. 7 illustrates an internal structure of the radiographic imaging apparatus according to the second embodiment of the present invention.

FIG. 6 illustrates an appearance (back side) of the radiographic imaging apparatus 100. FIG. 7 illustrates an internal structure of the radiographic imaging apparatus 100. FIG. 7 is a cross-sectional view taken along line B-B of FIG. 6. FIG. 8 illustrates a part of the internal structure of the radiographic imaging apparatus 100.

To ensure a high level of airtightness, the radiographic imaging apparatus 100 includes the sealing member 61 and a sealing member 62 between the front housing 1 and the back housing 2. A hole 60 is formed in a part of the back housing 2. The sealing member 61 and the sealing member 62 are elastic members, which have a valve shape in cross-section. The sealing member 61 and the sealing member 62 are attached to the edge of either the front housing 1 or the back housing 2. The sealing member 61 and the sealing member 62 are connected to form a single annular member, and can be regarded as a single sealing member. By assembling the front housing 1 and the back housing 2 together while compressing the sealing member 61 and the sealing member 62, airtightness at the contact between the front housing 1 and the back housing 2 of the housing can be maintained. A part of the sealing member 61 is of a special shape, and forms a valve (valve-shaped portion) that closes the hole 60 in the back housing 2.

The housing has a sealed structure formed by the sealing member 61 and the sealing member 62. However, the sealed structure may cause the housing to be deformed by changes in outside air pressure. Accordingly, it is preferable that the sealing member 61 and the sealing member 62 be in the shape of a valve. When the sealing member 61 and the sealing member 62 are valves, application of a given pressure raises the valves and allows passage of air. However, since the sealing member 61 and the sealing member 62 need to be subjected to a pressure to ensure airtightness, the direction of air passage is limited to a predetermined direction.

The hole 60 is provided in at least a part of the exterior of the housing. The hole 60 is formed as a through hole extending between the inside and the outside of the housing. The sealing member 61 is deformable. When a part of the sealing member 61 is shaped to cover the hole 60, this part allows outside air or inside air to pass therethrough. The sealing member 61 is configured to allow passage of air in a direction different from that in the other valve, so that a difference between the inside air pressure and the outside air pressure of the housing can be reduced.

Figure 8:
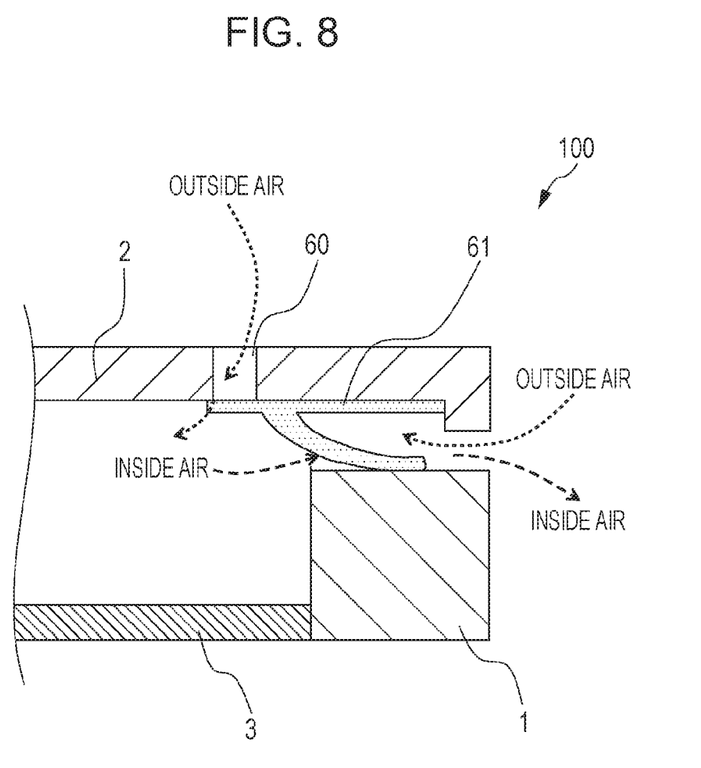
FIG. 8 illustrates a part of the internal structure of the radiographic imaging apparatus according to the second embodiment of the present invention.

Specifically, as illustrated in FIG. 8, outside air passes through the hole 60 and pushes the sealing member 61 covering the hole 60 to enter the housing. Inside air pushes the sealing member 61 between the front housing 1 and the back housing 2, or the sealing member 62 between the front housing 1 and the back housing 2, and is discharged to the outside of the housing. Since an air circulation cycle is thus formed in the radiographic imaging apparatus 100 (housing), a difference in air pressure between the inside and the outside of the radiographic imaging apparatus 100 can be reduced.

The sealing members described in the foregoing embodiments have a waterproof function. For example, the sealing members are made of silicone for use in medical equipment. In the case of selecting rubber as a material for the sealing members, the material to be selected is one that is less likely to be swollen and degraded by water or solvent used for cleaning. For example, fluorocarbon rubber, chloroprene rubber, NBR, or EPDM may be used.

The function described above may be achieved by using the sealing members formed of a resin material, such as elastomer. The shape and material of the sealing members are not limited to those described above.

Also, it is preferable that a material having a water repellent function and a waterproof function be selected to form components (battery holder 11, front housing 1, and back housing 2) in contact with the sealing members. Even when the sealing members are resistant to liquids, such as water, if the surrounding components are highly water-absorbing or water-attracting components, a liquid may penetrate through the sealing members. Accordingly, for example, a resin or metal having no water absorbency is selected as a material for the surrounding components.

The present invention is not limited to the embodiments described above, and can be variously changed and modified without departing from the spirit and scope of the present invention. The following claims are appended to disclose the scope of the present invention.

REFERENCE SIGNS LIST

1: front housing
2: back housing
3: radiation transmitting plate
4: shock absorbing member (protective sheet)
5: sensor (radiation detector)
6: shielding member
7: sensor retaining plate
8: electrical substrate
9: flexible cable
10: cover member
11: battery holder
15: battery
20: sealing member (first sealing member)
21: sealing member (second sealing member)
22: sealing member (third sealing member)

The invention claimed is:

1. A radiographic imaging apparatus comprising:
a radiation detector configured to detect radiation transmitted through an object to be examined and convert the radiation into an electrical signal; and
a housing configured to envelop the radiation detector, wherein the housing provides an incident plane configured to be irradiated with radiation, a back plane opposite to the incident plane, and a side plane connecting the incident plane and the back plane,
wherein an opening is disposed in the back plane, and a detachable cover member is attached to the opening and stationarily secured to the housing when attached,
wherein a sealing member is disposed inside the cover member to seal the opening, and
wherein the sealing member is a valve, which is configured to allow passage of air in a predetermined direction.

2. The radiographic imaging apparatus according to claim 1, wherein the housing and the sealing member form an air circulation cycle inside the housing.

3. The radiographic imaging apparatus according to claim 1, wherein the sealing member has a waterproof function.

4. The radiographic imaging apparatus according to claim 1, wherein the sealing member is disposed along a periphery of the cover member.

5. The radiographic imaging apparatus according to claim 1, wherein, when the cover member is attached to the opening, the sealing member is brought into contact with a battery holder configured to contain a battery.

6. The radiographic imaging apparatus according to claim 5, wherein the battery holder has a through hole extending from a space configured to contain the battery to a space inside the housing.

7. The radiographic imaging apparatus according to claim 1,
wherein the sealing member is a first sealing member, and
wherein a second sealing member is disposed on the housing.

8. The radiographic imaging apparatus according to claim 7, wherein the second sealing member is disposed along an edge of the opening in the housing.

9. The radiographic imaging apparatus according to claim 8, wherein the second sealing member is in contact with a battery holder configured to contain a battery.

10. The radiographic imaging apparatus according to claim 7, wherein each of the first sealing member and the second sealing member is a valve and are inclined in the same direction.

11. The radiographic imaging apparatus according to claim 1,
wherein the sealing member is a first sealing member,
wherein the housing includes a front housing and a back housing, and
wherein a third sealing member, having a function different from that of the first sealing member, is provided at a connection between the front housing and the back housing.

12. The radiographic imaging apparatus according to claim 11, wherein the third sealing member is for enhancing airtightness, and does not have the function of reducing a difference in air pressure between inside and outside of the housing.

13. The radiographic imaging apparatus according to claim 1, wherein the sealing member is made of silicon.

14. The radiographic imaging apparatus according to claim 1, wherein the sealing member is formed of a resin material.

15. The radiographic imaging apparatus according to claim 1, wherein the detachable cover is stationarily secured to the housing via one or more locking members.

16. The radiographic imaging apparatus according to claim 15,
wherein the one or more locking members is movable between a first position and a second position, and
wherein, in the first position, the detachable cover member is irremovable from the housing.

17. The radiographic imaging apparatus according to claim 16, wherein, in the second position, the detachable cover member is removable from the housing.

18. A radiographic imaging apparatus comprising:
a radiation detector configured to detect radiation transmitted through an object to be examined and convert the radiation into an electrical signal; and
a housing configured to envelop the radiation detector, wherein the housing provides an incident plane configured to be irradiated with radiation, a back plane opposite to the incident plane, and a side plane connecting the incident plane and the back plane,
wherein an opening is disposed in the back plane, and a detachable cover member is attached to the opening and stationarily secured to the housing when attached,
wherein a sealing member is disposed inside the cover member to seal the opening, and
wherein the sealing member is a valve, which is raised by a difference in air pressure between inside and outside of the housing.

19. A radiographic imaging apparatus comprising:
a radiation detector configured to detect radiation transmitted through an object to be examined and convert the radiation into an electrical signal; and
a housing configured to envelop the radiation detector, wherein the housing provides an incident plane configured to be irradiated with radiation, a back plane opposite to the incident plane, and a side plane connecting the incident plane and the back plane,
wherein an opening is disposed in the back plane, and a detachable cover member is attached to the opening and stationarily secured to the housing when attached, wherein a first sealing member is disposed inside the cover member, a second sealing member is disposed on the housing, and the first and second sealing members are configured to seal the opening, and wherein the first and the second sealing members are valves, which are configured to allow passage of air in a predetermined direction.

20. The radiographic imaging apparatus according to claim 19, wherein the first and the second sealing members are inclined in the same direction.

21. The radiographic imaging apparatus according to claim 19, wherein a battery holder configured to contain a battery is disposed in the opening.

* * * * *